United States Patent [19]
Andrus et al.

[11] Patent Number: 5,672,171
[45] Date of Patent: Sep. 30, 1997

[54] APPARATUS AND METHOD FOR INTERSTITIAL LASER TREATMENT

[75] Inventors: W. Scott Andrus; Mark Polyak; Sidney F. Hauschild, all of New York, N.Y.

[73] Assignee: American Medical Systems, Inc., Minnetonka, Minn.

[21] Appl. No.: 268,358

[22] Filed: Jun. 30, 1994

[51] Int. Cl.⁶ .................................................. A61B 17/36
[52] U.S. Cl. ............................ 606/15; 606/13; 606/16; 600/108
[58] Field of Search .................. 606/2, 3, 7, 10–16; 607/88, 89; 600/108

[56] References Cited

U.S. PATENT DOCUMENTS

| | | | |
|---|---|---|---|
| 4,207,874 | 6/1980 | Choy | 606/7 |
| 4,638,800 | 1/1987 | Michel | 606/16 |
| 4,819,630 | 4/1989 | De Hart | 606/15 |
| 4,950,267 | 8/1990 | Ishihara et al. | |
| 5,147,354 | 9/1992 | Boutacoff et al. | 606/3 |
| 5,169,396 | 12/1992 | Dowlatshahi et al. | 606/15 |
| 5,192,278 | 3/1993 | Hayes et al. | 606/7 |
| 5,195,541 | 3/1993 | Obenchain | 606/15 X |
| 5,290,279 | 3/1994 | Bonati et al. | 606/15 |
| 5,312,399 | 5/1994 | Hakky et al. | 606/15 |

FOREIGN PATENT DOCUMENTS

| | | | |
|---|---|---|---|
| 70459 | 7/1982 | European Pat. Off. | 606/16 |
| 2826383 | 12/1979 | Germany | 606/14 |
| 9210142 | 6/1992 | WIPO . | |

Primary Examiner—Angela D. Sykes
Assistant Examiner—Michael Peffley
Attorney, Agent, or Firm—Perer C. Richardson; Lawrence C. Akers; Mark Dryer

[57] ABSTRACT

An apparatus for delivering laser energy to a target through a radiation-transmitting waveguide having a distal end terminating in a tip which is in contact with the target during delivery, while protecting the tip from heat damage, which apparatus comprises a waveguide for transmitting laser radiation and having a distal end terminating in a tip adapted to be placed in contact with the target to deliver laser energy directly to the target at the site of contact, and means for delivering a controlled small amount of liquid to the target adjacent to the tip, which small amount is just sufficient to limit the temperature at the target to not more than the failure temperature of the tip. An apparatus assembly for performing ILC incorporating a waveguide and a method for protecting the tip of a waveguide from damage is also disclosed.

7 Claims, 7 Drawing Sheets

APPARATUS AND METHOD FOR INTERSTITIAL LASER TREATMENT

Field of Invention

This invention relates to an apparatus for delivering laser energy to a target, especially biological tissue; particularly when the laser energy is used for the interstitial treatment of benign prostatic hyperplasia (BPH). The invention is also concerned with a method for avoiding damage to a laser delivery apparatus, particularly an apparatus used for interstitial treatment of BPH.

Background to the Invention

BPH is commonly treated by open or transurethral surgery and the hazards associated with such treatment, i.e. morbidity, complications, and in some instances death, are well known. An alternative to conventional surgery is thermal treatment of the prostatic tissue with consequential elevation of the temperature above 37° C., the normal value. Various elevated temperatures are generally achieved. Tissue temperatures within the range of 42° to 45° C., designated by some practitioners as hyperthermia, result in some improvement in the treatment of BPH, but the procedure is protracted and may need to be repeated many times, and the results are not predictably satisfactory. At tissue temperatures within the range of 45° to 55° C., designated thermotherapy, treatment proceeds somewhat more rapidly with better results. When the temperature exceeds about 60° C., tissue undergoes an irreversible process of coagulative necrosis; and a single, relatively brief application of heat to produce such a temperature can alleviate BPH by reducing the size of the prostate.

Various methods of heating the prostrate to a temperature sufficient to cause coagulative necrosis have been investigated. For example, heat has been applied from a source in the urethra, but in this case damage to the urethral wall is common with the result that the symptoms of BPH are aggravated for a time of several months, even in those cases where eventual improvement is achieved. To avoid this effect and to achieve more acceptable results, BPH has been treated by the application of heat interstitially; i.e., by means of an energy-emitting device inserted into the prostatic tissue. In such a case, the energy-emitting device is typically the output tip of an optical fiber, although alternative devices, such as radio frequency or microwave antennae or other waveguides for delivering electromagnetic radiation, may be used. When the device comprises an optical fiber which transmits laser radiation, the temperature at the output tip of the fiber may rise well into the range for coagulative necrosis and will usually exceed 100° C.

As indicated above, interstitial laser coagulation (ILC) is a promising treatment for BPH. The treatment would be even more advantageous if the optical fiber could be delivered to the prostate by way of the natural passage through the urethra. However, a major difficulty arises from the need for a fiber with considerable mechanical flexibility.

In BPH the prostate gland comprises hyperplastic tissue which resides in two lateral lobes, located on either side of the urethra, and in a median lobe usually located in the bladder neck in line with the urethra. The urethra defines a generally straight path to the median lobe, which therefore may be treated by an instrument which is not particularly flexible. However, the lateral lobes are offset from the straight path and, consequently, placement, via a transurethral route, of an instrument, e.g. the tip of an optical fiber, in a lateral lobe is difficult and heretofore has not been successfully achieved. While a transrectal or transperineal route has been used, such a procedure is more invasive than the transurethral route and may have traumatic consequences. An additional advantage of the transurethral route is the ability to use an endoscope to observe the positioning of the fiber as it enters the prostate through the wall of the urethra. This cannot be done in a transpedneal procedure. Direct visualization is familiar and comfortable for the urologist and is a major advantage. Furthermore, the transurethral route allows the treatment of the median lobe as well as the lateral lobes.

International Patent Application No. WO 92/10142 discloses an apparatus for delivering laser energy to an organ adjacent to a body passageway which includes an optical fiber, a hollow needle for puncturing the passageway wall and organ and a catheter for delivering the optical fiber inside the needle to a position adjacent to the organ to be treated. To enable the fiber to pierce the urethral wall and be positioned within a lateral lobe it has to be highly flexible and the required flexibility is achieved by using a fiber having a core diameter not exceeding 400 μm. A commercially available cladded fiber with a core diameter of 400 μhas the required flexibility, but has a rated temperature limit of only 125° C. Thus, flexibility is achieved at the cost of using a fiber with less ability to withstand high temperatures, which limits the laser power that may be applied without risk of damaging the delivery system.

The power output of the system is critical because of the need to treat a large volume of tissue. The hyperplastic prostate may reach a volume exceeding 100 cc. in extreme cases; generally the volume is 30 to 50 cc. Desirably each affected lobe is treated individually with at least one burst of laser energy, with the goal of reducing the tissue mass of the lobe by several grams. Preferably, treatment by coagulative necrosis heats a volume of several cubic centimeters of prostate tissue to a temperature above 55° C. It is desirable that the tissue be heated to coagulation temperature as quickly as possible to avoid an unduly protracted procedure. A power of about 5 to 10 watts delivered through an optical fiber having a core diameter of 400 μm enables the required temperature for producing coagulative necrosis over the required volume to be reached within about five minutes. Smaller volumes may be treated in shorter times.

The progress of the laser-induced changes in the tissue may be observed directly using transrectal ultrasound (TRUS). This known method for imaging the prostate permits accurate monitoring and control of the laser procedure, which is particularly valuable since given laser energy doses may not produce equivalent effects in different individuals. Thus, the use of TRUS is an important safety feature.

If the power exceeds about 4 watts tissue near the tip of the fiber degenerates rapidly. Initially, the tissue reaches a temperature of 100° C., the vaporization temperature of water, and additional heat causes progressive drying of the tissue through vaporization of its contained water. There is no further temperature increase until the energy applied is equivalent to the latent heat of vaporization of the water to be evaporated. When all the water has vaporized the temperature of the tissues rises rapidly and charring of the tissue occurs. The charred tissue absorbs radiation strongly and thus is heated to still higher temperatures, which may reach hundreds of degrees. The fiber tip in contact with the tissue is similarly heated. Also, charred material may block the fiber's output tip; radiation is then absorbed within a tiny volume of the fiber, creating even higher temperatures. Tissue in contact with the fiber is burned and the fiber itself may be broken or melted, even when the fiber is quartz or fused silica which has a melting point over 1,600° C. The burning and resultant charred products are undesirable. Thus, using conventional techniques, the interstitial laser coagulation device described above can not consistently and safely deliver power greater than 4 watts for five minutes.

Thus, a widely recognized problem is the conflict between the need to limit the duration of the procedure by providing high power, and the power limitation imposed in interstitial procedures by the buildup of heat, charring, and damage to the delivery system in the tissue near the point of application of the energy, as well as possible changes in the thermal conductivity of the tissue. The problem is aggravated, when using the less traumatic transurethral route, by the need to use a small core diameter fiber with low heat capability to achieve the necessary flexibility to reach the lateral lobe via this path.

In order to reduce the power density from the fiber, and thus to avoid the problems described above, certain workers have devised tips that diffuse the energy from the optical fiber. But while these specialized fiber tip constructions do somewhat increase the power that may be safely delivered, they have disadvantages. They are difficult and expensive to manufacture. They are more bulky than the fiber itself, and thus take space that may be unavailable in the confined region of a prostatic lobe. Most importantly, they decrease the flexibility of the delivery system, making treatment of a lateral lobe via the transurethral route difficult if not impossible.

U.S. Pat. No. 5,169,396 discloses a method for interstitial laser therapy wherein a physiologically acceptable fluid that will establish a fluid pool in front of the fiber tip is applied to the region of tissue where the laser radiation is delivered. The fluid pool provides a heat transfer medium between the laser radiation and the tissue, thereby avoiding direct heating of the tissue. The fiber must be withdrawn at a constant rate during the procedure, keeping its tip in the pool and separate from tissue which might otherwise block the path of the radiation.

However, the above method has several disadvantages. It can not be used to produce widespread coagulative necrosis in the prostate because it generates a temperature no higher than 50° C. Such temperature is too low for rapid coagulative necrosis, as evidenced by the fact that the method treats only about 0.5 cc. of tissue per minute. An excessive amount of liquid is used, which slows the effect of the delivered energy and may present a physiological challenge to the patient. For example, when repeated doses are required, the recommended application of 1 cc/min. of liquid, preferably water, would apply 15 gm. of water in three 5-minute doses, which could easily exceed half the mass of the prostate itself. Because of the lower temperature caused by this use of excessive liquid, the duration of the dose and the amount of liquid administered would be even greater. Also, the immediate changes in the appearance of the tissue on TRUS during laser exposure result from drying of the tissue. When a high flow of liquid is used, the drying effect is masked and TRUS can not be used to monitor and control the procedure, leading to decreased safety and efficacy. Furthermore, withdrawal of the fiber at a constant rate requires additional equipment that may be unwieldy. The fiber has to be withdrawn a distance of about 10 mm in about 100 seconds. This low constant rate of 0.1 mm/sec. can not be achieved by hand and, according to the patent, is achieved by a lathe.

U.S. Pat. No. 4,950,267 discloses a laser beam treatment device for an endoscope which includes means for emitting ultrasonic waves and measuring the temperature at the site of treatment. The temperature at the treatment site is monitored by the reflected ultrasonic waves and controlled by adjusting the laser output accordingly. An embodiment in which cooling liquid is passed between the laser guide and a surrounding sheath is disclosed.

It has now been found that the disadvantages described above may be overcome and the safe treatment of BPH and other conditions may be achieved without trauma or excessive heating of tissue by a method and apparatus in which a controlled very small amount of liquid is applied to the tissue near the tip of the optical fiber as hereinafter described. Also, the presence of the small amount of liquid at the operational site may enhance the coagulation.

SUMMARY OF THE INVENTION

In accordance with the present invention there is provided an apparatus for delivering laser energy to a target, especially biological tissue, through a radiation-transmitting waveguide, preferably an optical fiber, having a distal end terminating in a tip which is in contact with the target during delivery, while protecting said tip from heat damage, which apparatus comprises a waveguide for transmitting laser radiation and having a distal end terminating in a tip adapted to be placed in contact with the target to deliver laser energy directly to the target at the site of contact, and means for delivering a controlled small amount of liquid to the target adjacent to said tip, said small amount being just sufficient to limit the temperature at the target to not more than the failure temperature of said tip.

The invention also provides a method for protecting the tip of a waveguide from damage during delivery Of laser energy transmitted through said waveguide to a target, which comprises contacting said target with said tip, transmitting laser radiation through said waveguide and to said target and, while laser radiation is being delivered, simultaneously delivering to the target adjacent the tip of the waveguide a controlled small amount of liquid, which amount is just sufficient to limit the temperature at the target to not more than the failure temperature of said tip.

The target usually treated by the method of the invention preferably comprises biological tissue, for example, prostatic tissue, and the usual object of the treatment is to produce coagulative necrosis of the tissue.

The invention further provides an apparatus assembly for performing interstitial laser coagulation (ILC) comprising, in combination, a delivery tool, a flexible cannula having a proximal end, a distal end, and outer and inner tubes which can be moved together and can slide axially with respect to each other, an actuator and a waveguide having a distal end and a proximal end, wherein the delivery tool comprises an elongated double lumen tube and a handle which includes a gripping portion and a rail, the double lumen tube comprises a first lumen adapted to receive and guide a viewing endoscope and a second lumen which accommodates the flexible cannula and waveguide and has a curved distal portion, the actuator comprises a slider and a trigger, the proximal end of the outer tube of the cannula being attached to the trigger and the proximal end of the inner tube of the cannula being attached to the slider so that movement of the trigger and slider produces corresponding movement of the outer and inner tube, respectively, the waveguide passing through a channel in the slider and into and through the inner tube of the cannula and a space between the waveguide and the inner tube defining a passageway for liquid to be delivered to the distal end of the waveguide.

The waveguide in the apparatus assembly is preferably a cladded optical fiber for delivering laser energy to perform the desired ILC, preferably on a patient's prostate.

The operation and function of the specific features of the apparatus assembly are described in more detail hereinafter.

DETAILED DESCRIPTION OF THE INVENTION

The waveguide used in the apparatus, method and apparatus assembly of the present invention is preferably a cladded optical fiber, and the invention will be more particularly described hereinafter with reference to preferred embodiments using an optical fiber.

A cladded optical fiber waveguide normally comprises a central optical fiber core which transmits electromagnetic radiation. Examples of suitable materials for the core are quartz, fused silica and polymers such as polymethyl methacrylate. The core is concentrically surrounded by a cladding which prevents leakage of laser radiation from the core so that substantially all the laser energy is delivered to the distal end of the waveguide and thus reaches the desired target. In the preferred waveguide used in the present invention the core and cladding are concentrically surrounded by an additional layer of material, herein designated as the buffer. The buffer is primarily included to provide mechanical strength to the waveguide.

The waveguide has a distal end terminating in a tip and when the waveguide comprises a cladded fiber with a buffer the cross-section of the tip has the appearance of three concentric members. Whether the waveguide is a single-membered radiation-transmission line or the preferred three-membered cladded optical fiber, any damage to the distal end or tip thereof is undesirable and, as used herein, the term failure of the tip means inability, including reduction of efficiency, of the tip to perform its desired function resulting from damage, particularly heat damage, to any one or more of the aforesaid members at the distal end thereof. Thus, in the preferred situation of a cladded optical fiber with buffer used to treat biological tissue, particularly the interstitial treatment of BPH, the failure temperature of the tip will be that temperature at which any one or more of the core, cladding and buffer is damaged by heat so as to produce charring, burning, melting or vaporization which affects the operational efficiency of the tip and/or contamination or infection of the operational site, surrounding tissue or other nearby body parts.

Clearly, if the distal end of the optical fiber core is damaged or destroyed, by melting or otherwise, this will lead to inefficient or diminished delivery of laser energy to the target. Also, if the cladding is damaged, so as to expose more of the core than the distal end in contact with the target, this will also reduce the efficiency of energy delivery. Furthermore, if the buffer is damaged the mechanical strength of the waveguide will be weakened making it more difficult to control the placement of the tip resulting in erratic operation. Even if the damage is such that there is minimal or no diminution of efficiency it would still be deleterious if it caused separation of pieces of the core, cladding or buffer from the tip, resulting in contamination of surrounding body parts. Any and all of the aforesaid circumstances are included within the definition of the term "failure" or "failure temperature" of the tip. Since the failure temperature is determined by the temperature at which the first of the materials used in the tip starts to melt or disintegrate, in practice the failure temperature will be the lowest melting point of the said materials, usually the plastic cladding or buffer, and such temperature is about 100° to 125° C. Thus, generally the controlled small amount of liquid used in the invention will be an amount just sufficient to limit the temperature at the target to not more than a temperature within the range of about 100° to 125° C. Also, the controlled small amount of liquid is preferably less than an amount which would materially limit temperatures more than about 10 min. from the fiber tip. The amount also should be less than an amount which would materially reduce the visibility on TRUS of the effect of the radiation on the tissue.

When the target is the preferred biological tissue, use of the apparatus or performance of the method of the invention has the primary effect of cooling the fiber tip and the tissue near the tip of the fiber, this being the tissue that otherwise would be heated to the highest temperature. Cooling avoids the destructive sequence of events initiated by charring near the fiber tip and resulting in failure of the tip, i.e., destruction of the delivery system and harm to the patient. The goals of cooling and protection of the fiber tip are achieved by the application of a very small amount of liquid, preferably physiological saline, to the tissue adjacent the tip of the optical fiber. The rate of application of the liquid is critical, since excessive liquid reduces the volume of tissue that undergoes coagulative necrosis and interferes with ultrasound monitoring, for example, TRUS monitoring. The amount of liquid applied is deliberately kept small, so that while it is sufficient to produce the enhancing effect described above, it does not form a pool that would dilute or weaken the effect of the laser radiation and unduly prolong the procedure. As a result, tissue more than about 10 min from the fiber tip is heated at about the rate that would prevail in the absence of liquid cooling. Energy from the laser radiation is delivered directly into the tissue since the tip of the optical fiber is maintained in direct contact with the tissue and yet the tip suffers no harm because the temperature of the tissue adjacent thereto is limited.

The invention will now be particularly described with reference to preferred embodiments wherein the waveguide in the apparatus and apparatus assembly is a cladded optical fiber and the target is biological tissue, for example, prostate tissue. In particular, the most preferred embodiment is an apparatus and method for interstitial treatment of BPH.

The preferred apparatus comprises a cladded optical fiber having a radiation-transmitting core made, for example, from quartz, fused silica or polymethyl methacrylate. The diameter of the core is about 400 μm. The core is surrounded by a cladding made, for example, from polyethylene. Around the cladding is a layer of a buffer made of plastic. The resulting three-member cladded fiber forms a waveguide having both mechanical strength and flexibility.

The waveguide is adapted to transmit laser radiation having a preferred wavelength within the range of about 810 nm to 1046 nm and a power output of 1.5 to 10 watts. Such radiation, when transmitted through the apparatus of the invention or used in the method of the invention for a period of about 5 to 10 minutes will produce the desired coagulative necrosis of tissue in the treatment of BPH.

The waveguide is usually accommodated within a disposable flexible cannula which is associated with a hollow tube or catheter which acts as a reusable delivery tool to deliver the waveguide to or near to the target or site of the treatment. Usually the cannula is mounted within the delivery tool.

The waveguide is preferably mounted within the cannula, both the waveguide and cannula being accommodated within the delivery tool. Preferably the cannula surrounds the waveguide and is adapted to transmit a physiologically-acceptable liquid and deliver a controlled small amount of the liquid to the region of the tip of the waveguide.

In providing means for delivering to the target adjacent the tip of the waveguide a small controlled amount of liquid, the apparatus includes not only the stated cannula but also a reservoir for the liquid and means for controlling the flow rate of the liquid from the reservoir to the cannula and thence to the tip of the waveguide so that the amount of liquid delivered to the target is just sufficient to avoid damage which would lead to failure of tip as described hereinabove but not so much as to impair the effectiveness of the treatment.

The preferred liquid used in the apparatus and method of the invention is physiologically-acceptable saline solution, hereinafter referred to simply as saline. The saline is initially at ambient room temperature of about 20° C. and is delivered through a cannula surrounding the cladded optical fiber and terminating in the plane of the fiber tip. The effect of the saline is to cool the tissue adjacent the output tip of the optical fiber.

The saline is delivered at a controlled flow rate that depends on the power of the laser radiation. As the laser energy heats the tissue, the saline is heated by contact with the nearby tissue to its vaporization temperature of 100° C. The saline is sufficiently transparent to the laser radiation (usually at a wavelength of about 1064 nm) that direct heating of the saline by laser radiation is relatively unimportant. As long as saline is present in the tissue at the tip of the fiber, the temperature of the tissue does not increase above about 100° C. Heating the saline from 20° C. to 100° C. requires 80 calories per gram of saline. Vaporization requires an additional 540 calories per gram, the latent heat of vaporization. Thus, to vaporize a gram of saline initially at 20° C. requires 620 calories. This is equivalent to 2591 joules, since one calorie is equivalent to 4.18 joules. If the laser power is W watts, the energy in joules delivered in one minute is 60×W, since the energy in joules is the product of power in watts and time in seconds. The mass of saline which may be vaporized in one minute by a laser power of W watts is therefore (60×W)/2591 grams. This is equivalent to a volume of (60×W)/2591 cc, since the density of water is 1 gr/cc. When W is 1 watt, a flow rate of 60/2591, equivalent to 0.023 cc/min or 23 µl/min, is enough to replace water lost to vaporization, and thus to limit the temperature to 100° C. For other values of W, the flow rate may be modified accordingly. In general, the flow rate required to ensure that not all of the water vaporized is at least 23×W µl/min, or 23 µl/min/watt. Preferably, the temperature is maintained at 100° C. until all the saline is vaporized or otherwise removed. Heat removes water from the tissue by vaporization and also by desiccation. Therefore, the minimum flow rate to maintain the tissue temperature at no more than 100° C. may be slightly above 23 µl/min/watt, as may be determined by simple experimentation. However, much higher flower rates are ineffective, for two reasons. A high flow rate may limit the desired effect of the laser radiation on the tissue by dampening too much of the laser energy. Accordingly, the flow rate should not exceed about four times the specified lower limit, i.e., it should be less than about 92 µl/min/watt. Additionally, if the flow rate is excessive, for example, more than about 600 to 800 µl/min at 10 watts, the TRUS image is unable to distinguish the extent of the laser radiation and the ability to use this tool to monitor and control the procedure is compromised according to experiments in vitro and in clinical trials.

Because the required flow rate is so low, it preferably may be provided by simple means, such as an inexpensive portable pump or a saline bag such as that found in most hospitals for intravenous administration.

Although described herein for the treatment of BPH, the procedure of the present invention involving cooling at low flow rates to preserve maximum effect and TRUS imaging capability, has wider applications; for example, in the treatment of tumors of the liver and other organs.

BRIEF DESCRIPTION OF DRAWINGS

The apparatus of the invention will be more particularly described with reference to preferred embodiments illustrated in the accompanying drawings, in which.

Figure 1:
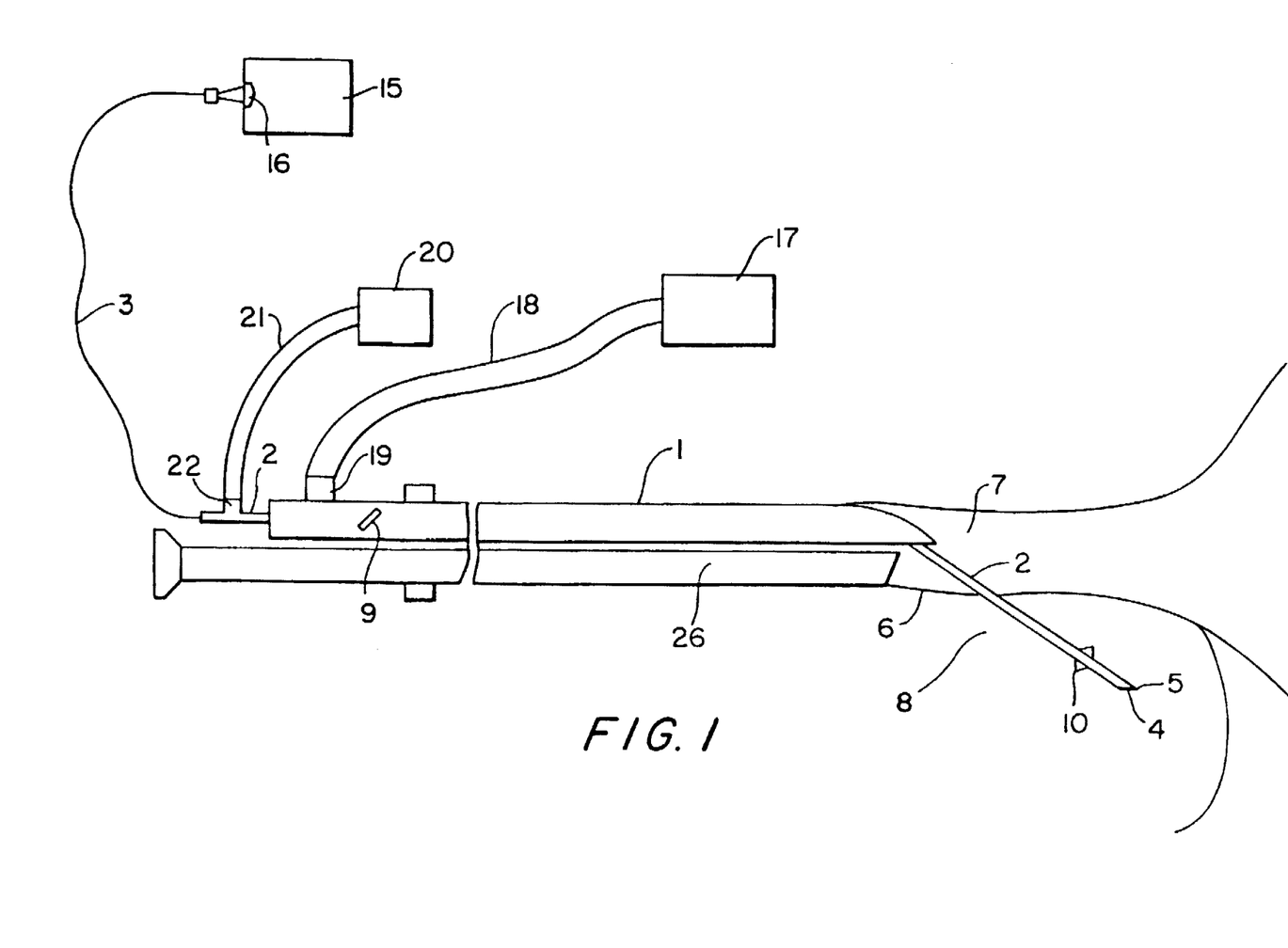
FIG. 1 is a schematic block diagram including a side elevation of an apparatus according to the invention in association with a telescope part of a urethroscope.

The embodiment illustrated in FIG. 1 of the accompanying drawings comprises a delivery or access tool in the form of an elongated tube 1 within which is accommodated a cannula 2 surrounding a radiation-transmitting waveguide comprising a cladded optical fiber 3. The distal end of the cannula is shaped into a bevel 4 having a sharp forward point 5 adapted to penetrate the wall 6 of the urethra 7 when the instrument is inserted in the urethra and the cannula emerges from the distal end of the access tool 1. The cannula is preferably made from a plastic material or thin stainless steel and penetration of the urethral wall is aided by the bevelled shape of the distal end. After penetration of the urethral wall the bevelled end of the cannula enters the parenchyma of the prostate 8. A deployment switch 9 on the access tool is actuated to cause deployment of an anchor 10 comprising lateral protuberances on the side wall of the cannula, near to but set back from the distal bevelled end. The anchor prevents movement of the cannula and waveguide once the tip of the waveguide is placed in contact with tissue at the treatment site of the prostate. An alternative, preferred, mechanism for deploying an anchor is described in more detail with reference to the embodiment illustrated in FIG. 10.

Figures 2, 2A, 3:
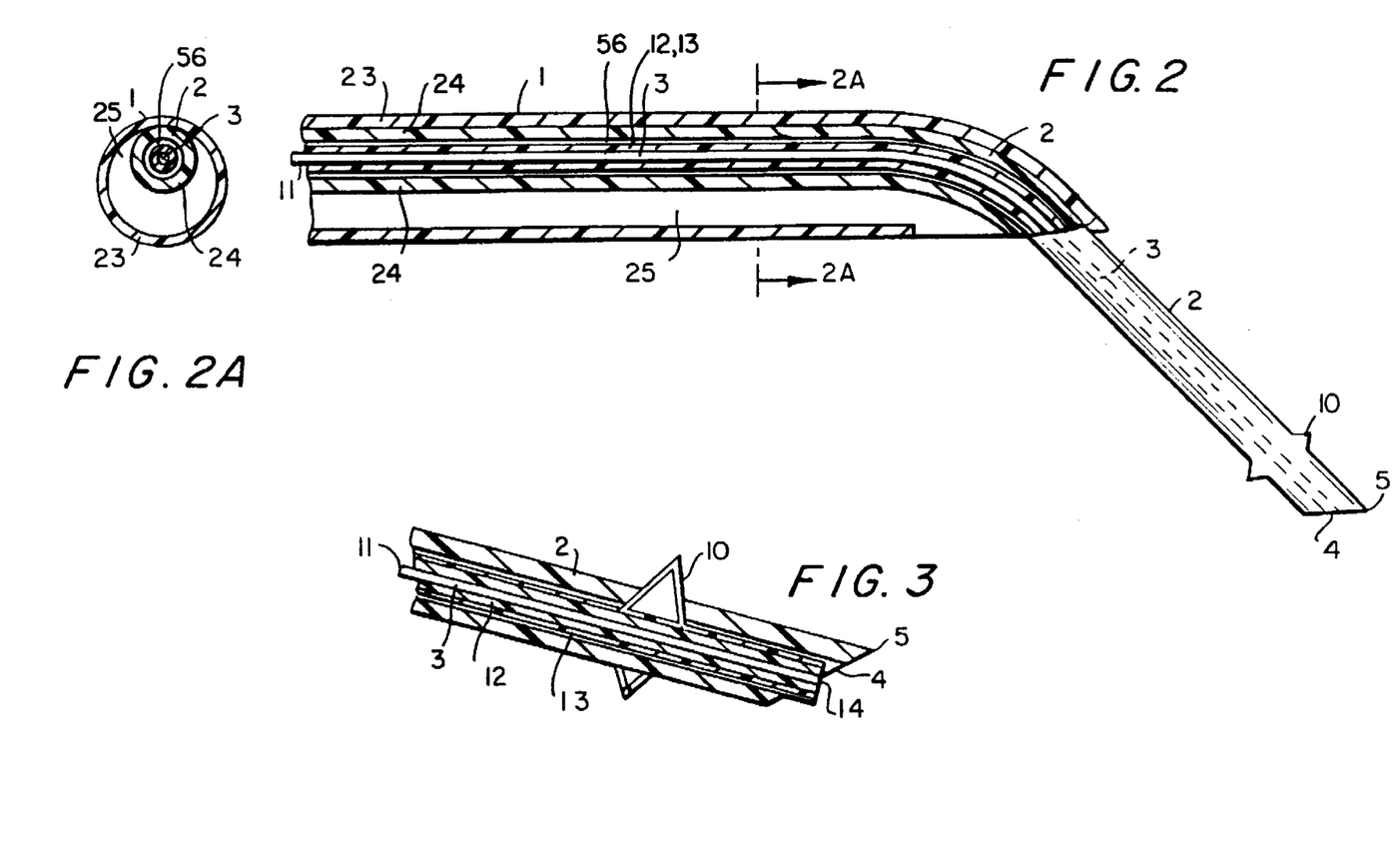
FIG. 2 is a sectional side elevation of part of a preferred embodiment of the invention.
FIG. 2A is a cross-section across line A—A of FIG. 2.
FIG. 3 is a enlarged view of the distal end of the apparatus of FIG. 2.

As shown in more detail in FIG. 2 and FIG. 3 the waveguide 3 comprises an optical fiber core 11 surrounded by a concentric cladding 12 which, in turn, is surrounded by a concentric buffer 13. The distal end of the waveguide terminates in a tip 14 which partially projects from the bevelled end of the cannula.

The proximal end of the waveguide is connected to a source of laser radiation 15 and laser energy is focused into the optical fiber through a beam focusing lens 16. A preferred laser which produces energy of a suitable wavelength for the interstitial treatment of BPH is a neodymium/ yttrium-aluminum-garnet (Nd:YAG) laser. Saline from an irrigation supply reservoir 17 is introduced into the access tool, through a pipe 18 and an entry port 19 at the proximal end of the access tool, to irrigate the urethra.

It is to be understood that the means for deployment of fiber optic elements and means for delivering laser energy and irrigation means, is known in the art and a similar arrangement is disclosed, for example, in International Patent No. WO92/10142. Means for anchoring the apparatus is also known in the art.

Cooling saline from a reservoir 20 at room temperature is introduced into the cannula through a pipe 21 and a port 22 at the proximal end of the cannula. The cooling saline passes through a channel 56 in the cannula around the cladded optical fiber. The rate of flow of the cooling saline is carefully controlled by means, such as a simple pump (not shown) or by careful positioning of the reservoir 20, which may be a saline bag with an appropriate valve, which provides a small controlled amount of saline just sufficient to limit the temperature of the tissue in contact with the tip to not move than the failure temperature of the tip. If desired, the pump or other flow control means may be provided with means (not shown) which emits a warning when the desired pressure, indicative of the correct flow rate, is exceeded. The saline is delivered from channel 56 directly within the prostatic parenchyma to the site of the treatment.

FIG. 2 is a somewhat enlarged sectional side elevation of the distal portion of the access tool 1 which comprises an outer wall 23 and an inner wall 24. The inner wall accommodates the cannula 2 containing the waveguide 3. The space between the outer wall 23 and inner wall 24 defines an irrigation channel 25 (see FIG. 2A) which carries saline from reservoir 17 for irrigating the urethra 7. This channel is also adapted to accommodate an endoscope and, when the scope is in place, the irrigation channel is defined by the space between the outside wall of the scope and the outer wall 23 of the tool.

Figure 4:
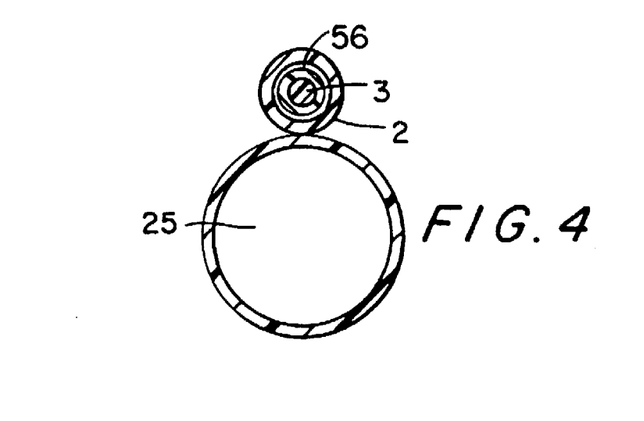
FIG. 4 is a cross-section of an alternative embodiment to that of FIG. 2A.
Figure 5:
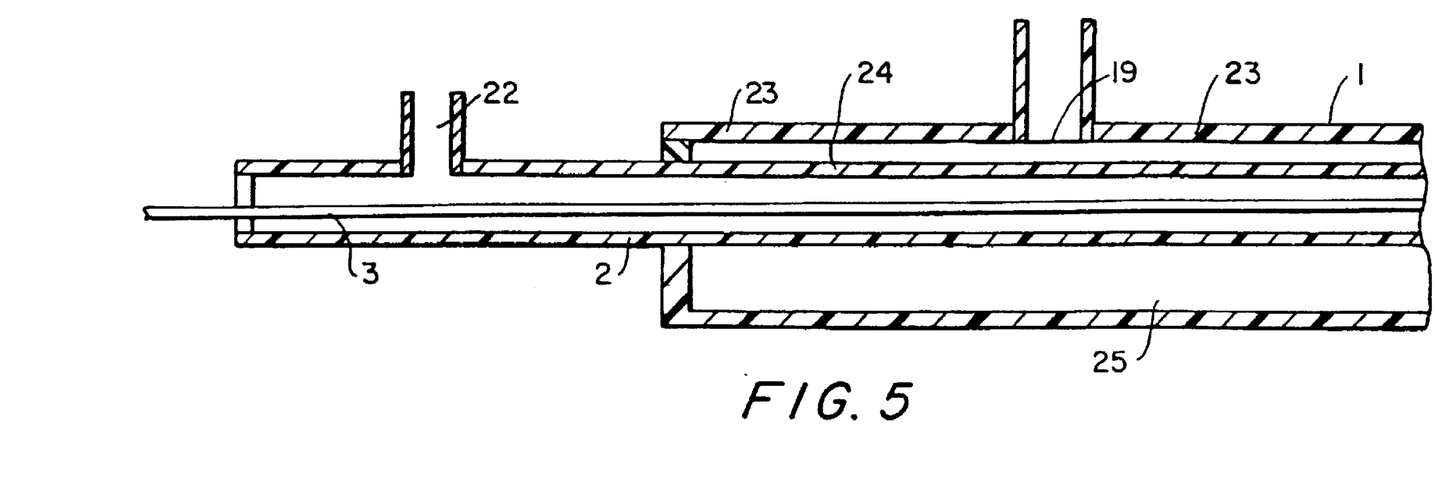
FIG. 5 is an enlarged side section of the proximal end of the delivery tube of the apparatus of FIG. 1.

An alternative embodiment wherein the irrigation channel 25 is mounted alongside the cannula 2 rather than around it is shown in FIG. 4. An advantage of this alternative embodiment is that it is easier to clean. In both embodiments the access tool directs the cannula at an angle when it is deployed from the tool. During insertion of the tool into the urethra, the cannula and waveguide are pulled back into the tool. After insertion the cannula and waveguide are advanced beyond the distal end of the access tool and are deployed at an acute angle of above about 30°.

The embodiment illustrated in FIG. 1 is completed by a telescope 26 mounted alongside the access tool. The telescope may be the optical part of a standard cystoscope or urethroscope and is included for visualization of the urethra to enable the operator to correctly position the cannula within the parenchyma of the prostate.

Figure 6:
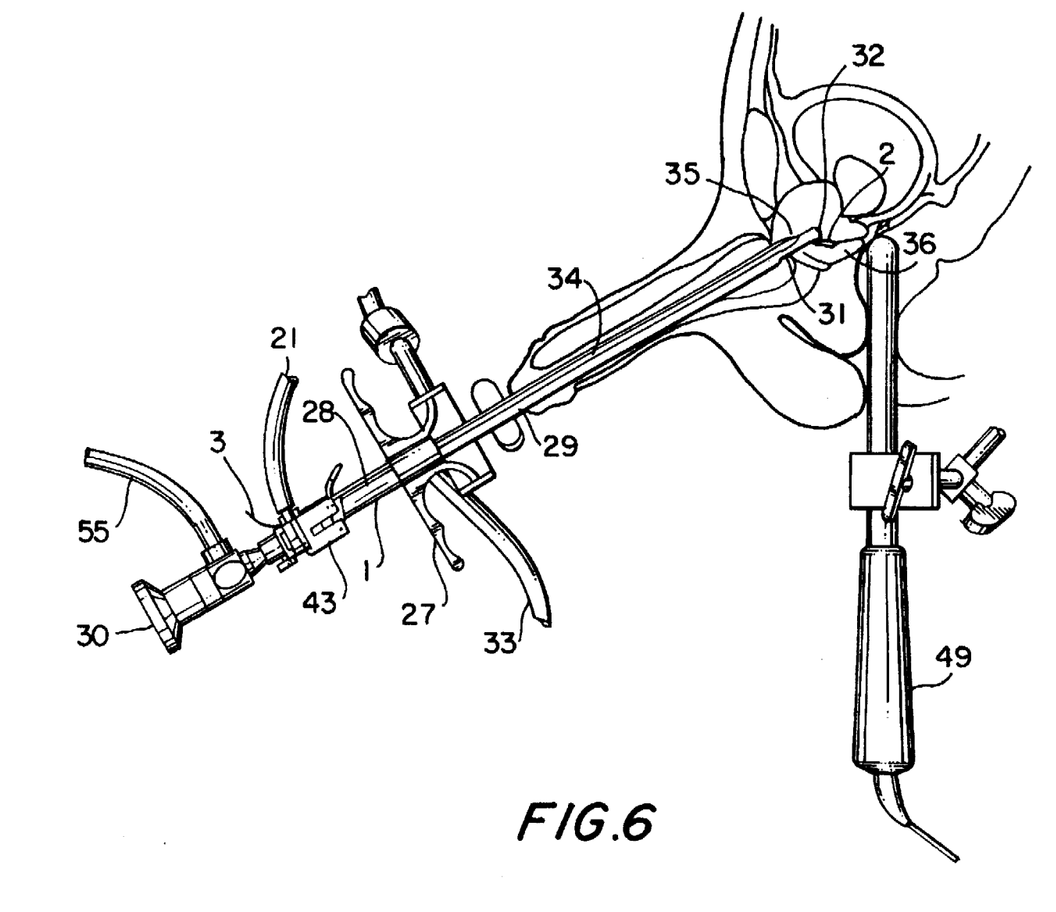
FIG. 6 is a perspective view of an apparatus assembly according to the invention in its operational position within a patient's urethra.
Figure 7:
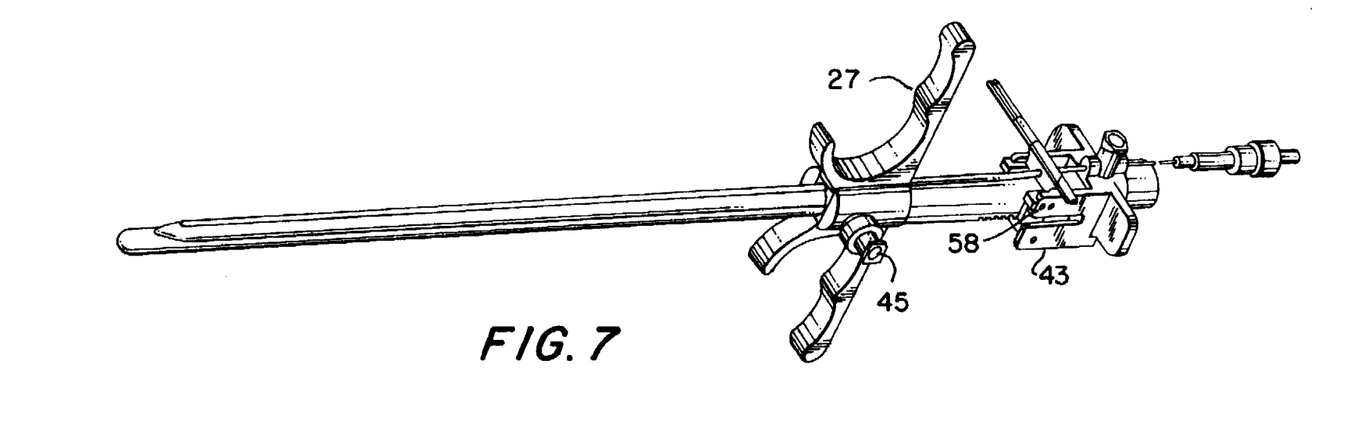
FIG. 7 is a perspective view of the delivery tool and cannula combination of the apparatus assembly of FIG. 6.
Figure 8:
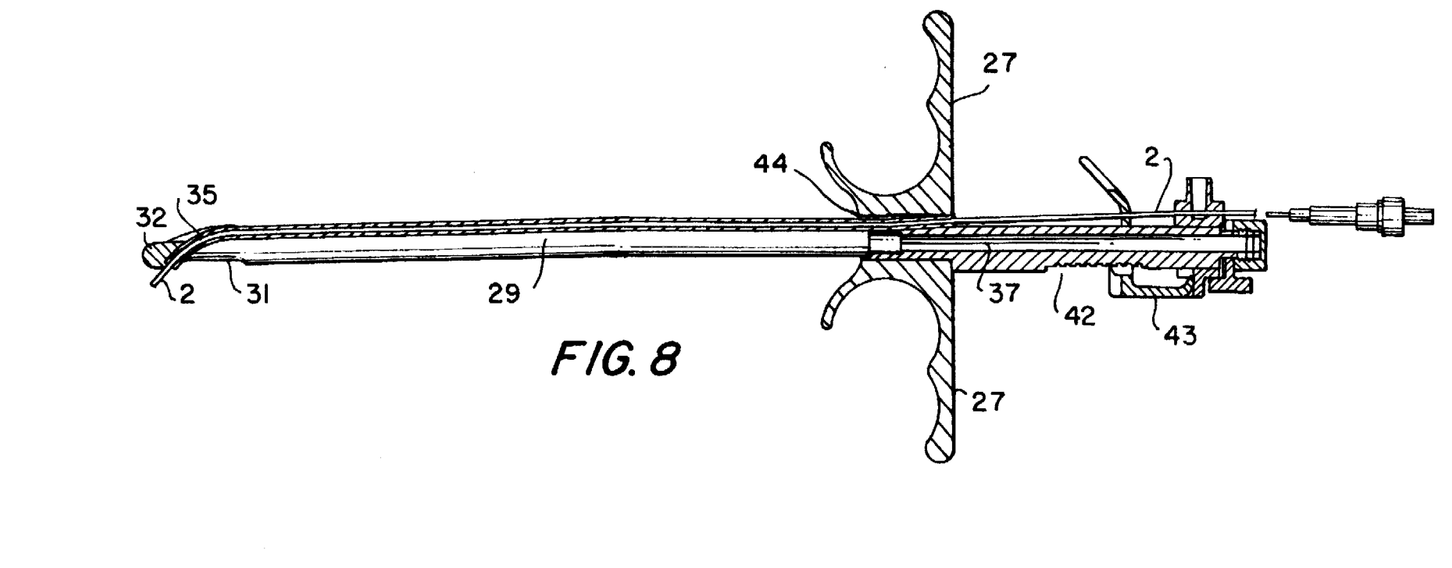
FIG. 8 is a side elevation, partly in section, of the delivery tool/cannula combination.
Figure 12:
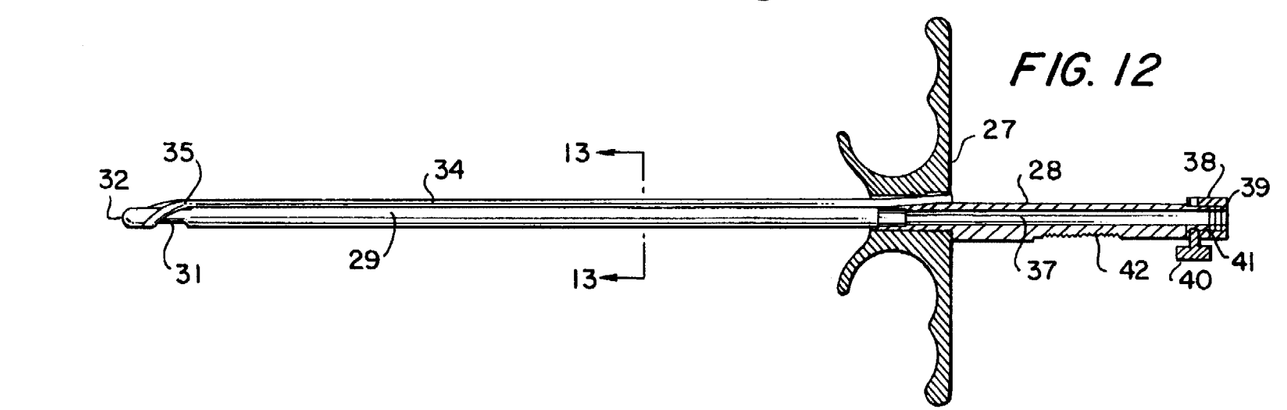
FIG. 12 is a side elevation, partly in section, of the tool of FIG. 11.
Figure 13:
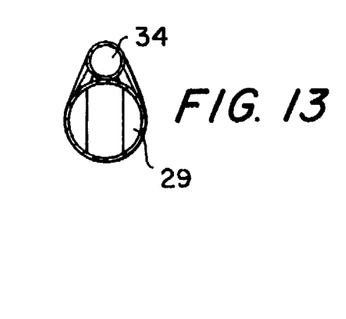
FIG. 13 is a cross-section through line (13)—(13) of FIG. 12.

The apparatus assembly illustrated in FIG. 6 comprises a reusable delivery tool 1 which has an elongated double lumen tube and a handle 27 which includes a gripping portion 27 and a rail 28 (see FIG. 12). The larger diameter first lumen 29 of the double lumen tube receives and guides a viewing endoscope having an eyepiece 30 at its proximal end. At the distal end of the lumen side wall, there is a rectangular window 31 defining a viewing port for the scope. The distal end 32 of the lumen is plugged. A gap between the outer wall of the scope and inner wall of the lumen serves as a passageway for irrigation water introduced through pipe 33. The viewing port 31 provides an opening for irrigation water outflow. A second smaller diameter lumen 34 receives and guides a flexible disposable cannula 2 with a fiber 3. The second lumen is adjacent to the outside wall of the first lumen and its location is opposite to the viewing port. The distal portion 35 of the second lumen is curved in order to direct a flexible cannula 2 and fiber tip into the tissue 36 to be treated, i.e., the prostate tissue. The curved portion crosses the distal end of the first lumen and stops at the viewing port. Therefore, the distal end of the curved portion can be viewed through the scope. The proximal end of the double lumen tube is attached to the gripping side of the tool handle. The rail 28 extends from the gripping portion of the handle opposite to the double lumen tube. A longitudinal bore 37 in the rail and gripping portion is a continuation of the first lumen. The bore and the first lumen coincide axially. The proximal end of the bore defines an entrance port for an endoscope. When a collar 38 with a seal 39 inside is tightly engaged, with the help of a locking thumbscrew 40, with a threaded portion 41 of the proximal end of the rail, it locks a scope in the longitudinal and angular position in the tool and provides a liquid tight seal around the scope. Transverse grooves 42 on the bottom surface of the rail enables an actuator 43 for the cannula to be locked on the tool rail. An aperture 44 on the gripping portion of the handle is an entrance port for the flexible cannula 2 into the second lumen of the double lumen tube. The irrigation-aspiration port 45 (FIG. 7) for irrigation water on the handle is equipped with a female luer connector.

The cannula assembly, which is disposable, consists of a flexible cannula 2, an actuator 43 and a laser optical fiber 3. The cannula includes flexible coaxial outer 46 and inner 47 tubes (FIG. 10), which can slide with respect to each other. At the distal end 48, the tubes are bonded together over the short portion. A piercing point 5 at the cannula tip is made by cutting the bonded portion at an angle. Echogenecity of the bonded portion is enhanced to facilitate positioning of the cannula in the tissue under an ultrasound probe 49. The cannula has a locking anchor 10 adjacent to the bonded portion. The deployed anchor locks positions of the cannula and laser fiber tips in the tissue to be treated. The anchor comprises a portion of cannula outer tubing with longitudinal slits, which allow outward extension of that portion in response to an axial movement of the outer tube with respect to the inner tube.

Figure 9:
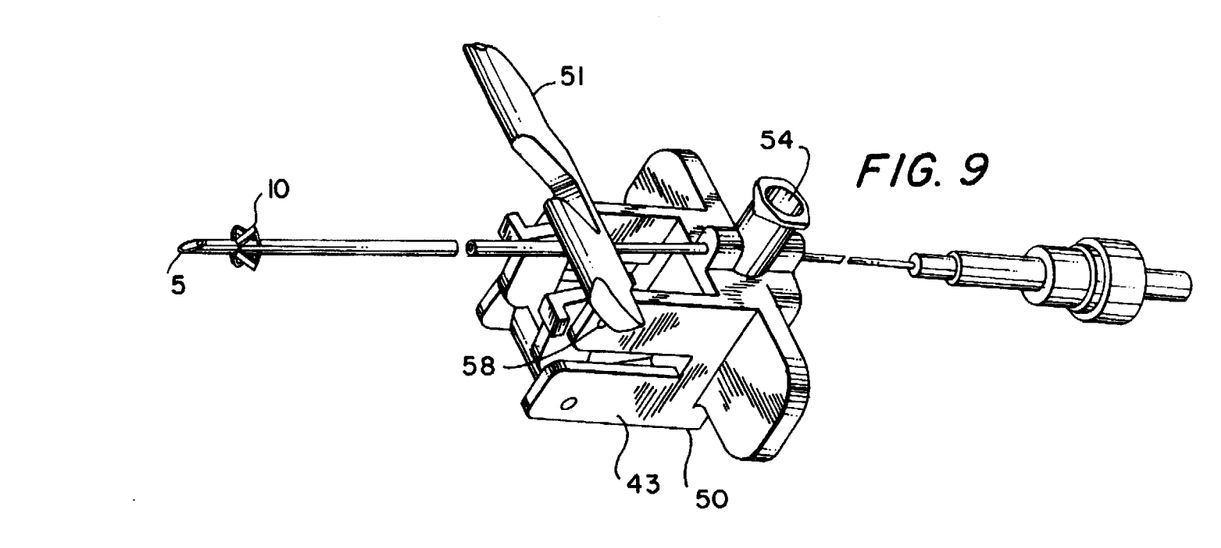
FIG. 9 is a perspective view of a trigger/slider mechanism of the apparatus assembly.
Figure 10:
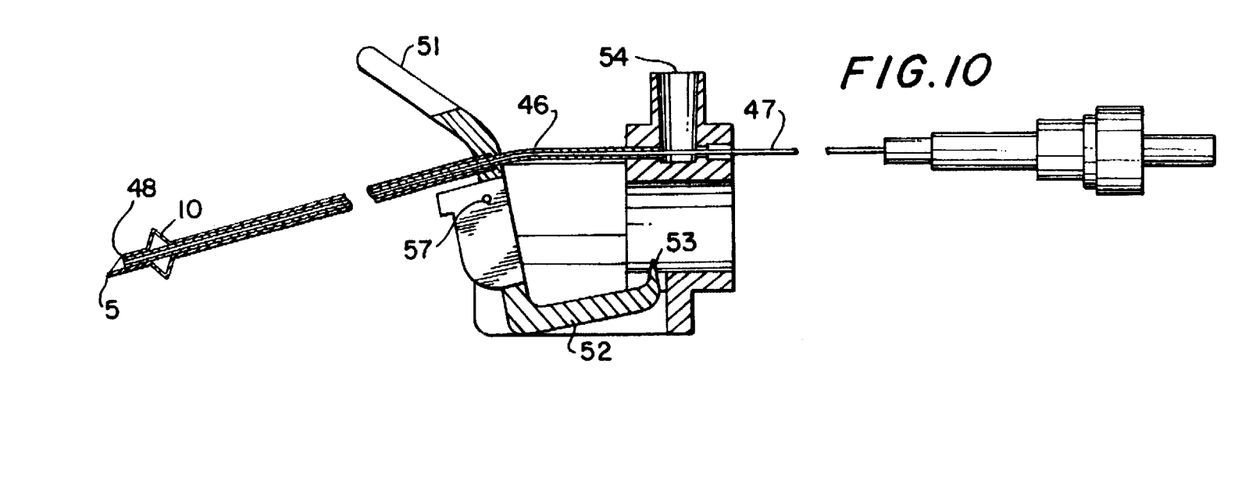
FIG. 10 is a side elevation, partly in section, of the mechanism of FIG. 9.
Figure 11:
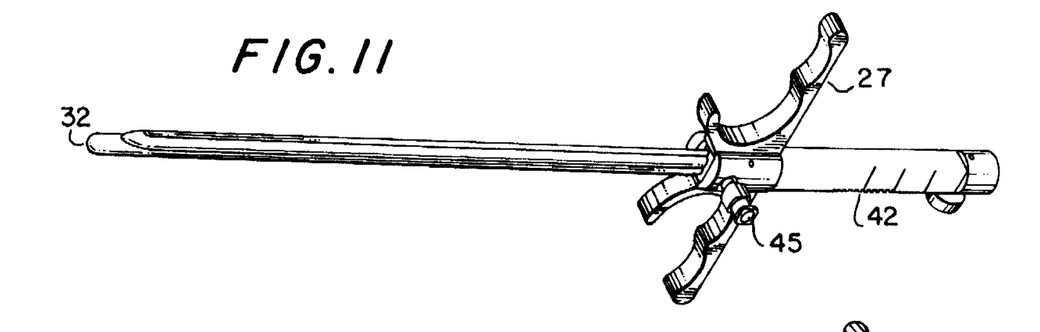
FIG. 11 is a perspective view of the delivery tool.

The actuator 43 of the cannula assembly generates the axial movement. The actuator is illustrated in FIG. 9 and includes a slider 50 and a trigger 51. The trigger pivots in the slider between forward and backward fixed positions. The forward position is shown in FIG. 10. The positions are fixed by snap means, which consists of a bump 57 on each side of the trigger and two holes 58 on each flexible arm of the slider. The bumps when they are engaged with the holes, provide a snap type fixation to the trigger pivoting position in the slider. The trigger has a locking arm 52 with a tooth 53. The proximal end of the cannula outer tube is bonded to the trigger and the proximal end of the inner tube is bonded to the slider. Movement of the actuator as a whole, i.e., the trigger and slider together, moves both tubes of the cannula forward or backward as the case may be. Pushing the trigger in the forward fixed position generates an axial movement of the outer tube relative to the inner tube and deployment of the anchor. At the same time, the tooth of the trigger locking arm engages with the rail grooves 42 and locks the actuator on the rail. To retract the anchor and unlock the actuator, the trigger should be pulled to the backward position. The snap means of the actuator controls the amount of force required to deploy and retract the anchor. A laser optical fiber 3 passes through a channel in the slider into and through the inner tube of the cannula. The distal tip of the fiber coincides with the cannula tip. The fiber is bonded to the slider. A space between the optical fiber and the inner wall of the inner tube of the cannula defines a passageway, corresponding to passageway 56 in FIG. 2 and FIG. 3, for liquid supply to cool the fiber tip. There is an inlet port 54 for the cooling liquid in the slider. The port is in communication with the cannula passageway and equipped with a female luer connector. An axial rectangular bore in the slider and trigger guides the actuator when it slides on the tool's rail. Viewing through the scope is facilitated by light introduced through a light cord 55.

To use the apparatus assembly for an ILC procedure, the following steps should be followed:

1) The reusable delivery tool is assembled with the cannula assembly by inserting the cannula into the second lumen and sliding the cannula actuator on the tool rail.
2) The collar is assembled with the threaded end of the rail.
3) A 30° scope is inserted in the first lumen of the delivery tool and locked in the tool by tightening the collar and the collar set thumb screw.
4) The irrigation/aspiration port of the tool is connected to a source of irrigation liquid. A connecting tube should be equipped with a male luer connector and a 3-way stopcock valve.
5) The liquid inlet port of the cannula actuator is connected to a cooling liquid pump through a tube with a male luer connector.
6) The scope is connected to a light source by the light cord 55.
7) The required power is chosen from a laser which is calibrated with a separate fiber and the optical fiber in the cannula is connected to the laser.

The assembled apparatus is checked as follows:

a) The view is inspected through the scope and, if necessary, the scope position in the tool is adjusted.
b) The cooling liquid pump is turned on and the liquid supply to the cannula/fiber tips is verified.
c) The stopcock valve (not shown) is turned on and the irrigation liquid supply is verified.
d) The slider is pushed distally until the tip of the cannula is deployed out of the tool at least 10 mm. The anchor is deployed and locking of the actuator on the tool rail is checked. After the procedure is completed the anchor is released and the cannula is retracted back into the tool.

For proper deployment as described above, clearly the cannula has to be made of a flexible material, preferably a plastic material or thin malleable stainless steel. Thus a rigid metal cannula, such as that used in the apparatus disclosed in U.S. Pat. No. 5,169,396, could not be used in the present invention. The need for flexibility results in the need for cooling, since materials which can tolerate high temperatures do not have the desired flexibility. Thus the provision of an apparatus having a flexible waveguide capable of delivering high power according to the present invention may be considered to be predicated by the need to provide cooling to prevent destruction of the tip of a flexible material.

We claim:

1. An apparatus assembly for performing interstitial laser coagulation comprising, in combination, a delivery tool, a flexible cannula having a proximal end, a distal end, and outer and inner tubes which can be moved together and can slide axially with respect to each other, an actuator and a waveguide having a distal end and a proximal end, wherein the delivery tool comprises an elongated double lumen tube attached to a handle which includes a gripping portion and a rail wherein the double lumen tube is attached to one side of said gripping portion of the handle and the rail extends from a side of the gripping portion opposite to the double lumen tube, the double lumen tube comprises a first lumen adapted to receive and guide a viewing endoscope and a second lumen within which the flexible cannula and waveguide are accommodated longitudinally and which has a curved distal portion, the actuator comprises a slider with two flexible arms and a trigger, wherein the trigger has two sides which pivot in the slider between forward and backward fixed positions, each of which positions is fixed by snap means consisting of a bump on each side of the trigger and a cooperating hole on each flexible arm of the slider, the proximal end of the outer tube of the cannula being attached to the trigger and the proximal end of the inner tube of the cannula being attached to the slider so that movement of the trigger and slider produces corresponding movement of the outer and inner tube, respectively, the waveguide passing through a channel in the slider and into and through the inner tube of the cannula and a space between the waveguide and the inner tube defining a passageway for liquid to be delivered to the distal end of the waveguide.

2. An assembly according to claim 1 in which the delivery tool is made of a sterilizable material and is reusable, the cannula is disposable and the combination of tool and cannula is sized for the treatment of a patient's prostate.

3. An assembly according to 2, in which the waveguide is a cladded optical fiber.

4. An assembly according to claim 3 which includes means for locking an endoscope within the first lumen of the delivery tool.

5. An assembly according to claim 1 in which the rail has transverse grooves on a bottom surface which permit the actuator to be locked on the rail by engagement of a tooth on the actuator with one of said grooves.

6. An assembly according to claim 1, in which the cannula has an anchor adjacent its distal end, which anchor comprises lateral protuberances on the inner tube and longitudinal slits in the outer tube which allow deployment of said protuberances when the outer tube is moved axially with respect to the inner tube by means of the slider and trigger.

7. An assembly according to claim 1, in which the distal end of the waveguide terminates in a tip and the passageway for delivering liquid to the tip is attached to means for delivering a controlled small amount of liquid to said tip, said small amount being just sufficient to limit the temperature at the tip to not more than the failure temperature of said tip.

* * * * *